United States Patent [19]
Wright

[11] Patent Number: 4,627,272
[45] Date of Patent: Dec. 9, 1986

[54] VISCOMETER

[75] Inventor: Hubert A. Wright, Cambridge, Mass.

[73] Assignee: Cambridge Applied Systems, Inc., Cambridge, Mass.

[21] Appl. No.: 675,536

[22] Filed: Nov. 28, 1984

[51] Int. Cl.$^4$ .................... G01N 11/12
[52] U.S. Cl. .................... 73/57; 73/54
[58] Field of Search .................... 73/54, 57

[56] References Cited

U.S. PATENT DOCUMENTS

| 1,790,948 | 2/1931 | Rodgers | 73/57 |
| 2,957,338 | 12/1960 | Kennedy et al. | 73/54 |
| 3,073,150 | 1/1963 | Fann | 73/54 |
| 3,073,151 | 1/1963 | Fann | 73/54 |

FOREIGN PATENT DOCUMENTS

| 611575 | 12/1960 | Canada | 73/57 |
| 486249 | 1/1970 | U.S.S.R. | |
| 693154 | 11/1979 | U.S.S.R. | 73/57 |
| 1092380 | 3/1982 | U.S.S.R. | |

*Primary Examiner*—Stewart J. Levy
*Assistant Examiner*—Hezron E. Williams
*Attorney, Agent, or Firm*—Cesari and McKenna

[57] ABSTRACT

A viscometer (10) employs a tube (12) with a check valve (30) at one end and a ferromagnetic bobbin (16) disposed inside and freely movable with respect to it. A pair of coils (38 and 40) are alternately energized, causing the bobbin (16) to move against fluid in the tube in one direction, in which the check valve (30) prevents fluid flow, and in the other direction, in which the check valve (30) permits fluid flow within the tube. When the bobbin (16) moves in the direction in which the check valve (30) permits flow, it draws a new sample of fluid into the tube, and the time required for the bobbin (16) to move in the other direction, in which fluid flow is prevented by the check valve (30), is measured as an indication of the viscosity of the fluid. The position of the bobbin is sensed by measuring the mutual inductance between the coils (38 and 40). Preferably, the bobbin (16) is of neutral buoyancy so that operation of the viscometer is substantially insensitive to vibration and to orientation with respect to gravity.

23 Claims, 12 Drawing Figures

COIL
DRIVE CURRENT

COIL B
E.M.F.

— VOLTAGE-DIVIDER OUTPUT
-- ENVELOPE OF COIL E.M.F.

COMPARATOR 78 OUTPUT 2.2 TO
ONE-SHOT 84 OUTPUT

ONE-SHOT 86 OUTPUT

BTA

VISCOMETER

BACKGROUND OF THE INVENTION

The present invention is directed to the field of viscometers. It finds particular application in viscometers used to sense viscosity remotely.

The viscosity of a fluid is important in many situations. In the installation of oil-well casings, for instance, it is often important to know the viscosity of the concrete used for that purpose. In such situations, it is easy to take a sample of the concrete manually, and the sample is manually placed in a viscometer that indicates the viscosity of the concrete.

There are other situations, however, in which, although the viscosity of a fluid is important, viscosity measurement has in the past been too inconvenient to perform routinely. In large earth-moving equipment, for example, changing lubricating oil involves some expense and inconvenience, so a fixed oil-change schedule in which oil changes are too frequent adds to the cost of operation. However, conservative operation requires that the changes be relatively frequent because small changes in temperature or other operating conditions can greatly reduce the life of the lubricating oil, and an oil-change schedule that ordinarily is more than frequent enough can become far too infrequent if conditions change. Since it is possible by measuring viscosity to determine when the time has arrived to change the oil, it would be desirable to change oil only when a measurement of viscosity indicates that an oil change is necessary.

But such measurements are inconvenient. It is time-consuming to take an oil sample for testing outside of the machine on a frequent basis. While it is theoretically possible to employ a dedicated viscometer permanently installed in the machine and providing a remote viscosity indication, existing viscometers do not meet the requirements of simplicity, reliability, and insensitivity to orientation and vibration required in such an application.

It is accordingly an object of the present invention to enable viscosity to be measured remotely by employing a simple device that is relatively insensitive to orientation changes and vibrations.

SUMMARY OF THE INVENTION

The foregoing and related objects are achieved in a viscometer that includes means such as a tube for defining a chamber that contains the fluid whose viscosity is to measured. A ferromagnetic bobbin is disposed in the chamber and is free to move back and forth through the fluid in the chamber. Two coils are mounted in separate locations on the tube to draw the bobbin in one direction or the other, depending on which coil is energized.

Circuitry is provided for driving one of the coils with an alternating current to pull the bobbin toward it and induce an electromotive force in the second coil. Movement of the bobbin causes a change in the mutual inductance between the coils, and this results in a change in the amplitude of the electromotive force observed in the second coil. Accordingly, it is possible to determine when the bobbin has moved to a predetermined position near the first coil. When this point is reached, the second coil is driven to pull the bobbin back to a position adjacent to the second coil, and the sequence is then repeated. By measuring the time required to move from the second coil to the first coil, it is possible to deduce the viscosity of the fluid within the tube.

In accordance with one aspect of the invention, the tube is open at the end near the second coil, and fluid flow at the other end is controlled by a check valve. When the bobbin moves from the first coil toward the second coil, the check valve permits fluid to be drawn into the tube by bobbin motion, but the check valve prevents flow out of the tube when the bobbin moves in the other direction. In this way, there is enough resistance to fluid flow to permit an accurate viscosity measurement when the bobbin moves in one direction, but movement in the other direction pumps fluid into the chamber to update the fluid sample.

In accordance with another aspect of the invention, the bobbin is arranged to have substantially neutral buoyancy. As a consequence, the operation of the viscometer is substantially insensitive to gravitational effects caused by changes in orientation, and it also is largely insensitive to vibration. It is thus suited to use in locations, such as in the crankcases of earthmoving equipment, in which vibrations and changes and orientation are likely to be encountered. Furthermore, because of its simple construction, it affords the high reliability required of a remote sensor.

BRIEF DESCRIPTION OF THE DRAWINGS

These and further features and advantages of the present invention are described in connection with the accompanying drawings, in which.

DETAILED DESCRIPTION OF THE PREFERRED EMBODIMENT

Figure 1:
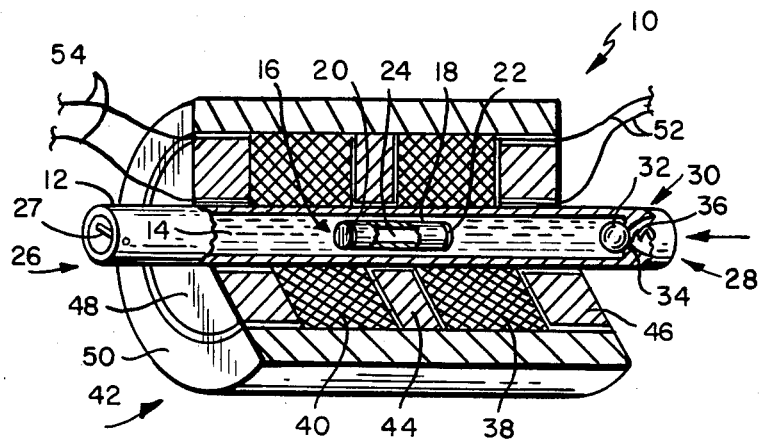
FIG. 1 is a front elevation, partially in section, showing the viscometer of the present invention.

FIG. 1 depicts a viscometer 10 that embodies the teachings of the present invention. The viscometer 10 includes an elongated tube 12 that defines a chamber 14. Inside the chamber 14 is disposed an elongated bobbin 16 for which the tube 12 acts as a guide. The bobbin 16 comprises a cylinder 18 of ferromagnetic material with end caps 20 and 22 at opposite ends made of molded metal or epoxy. The end caps enclose an air space 24 within the bobbin. The ratio of the volume of the air space 24 to that of the ferromagnetic material and end caps is such that the average density of the bobbin is the same as the expected density of the fluid to be measured, so the bobbin 16 has substantially neutral buoyancy.

The tube 12 has an opening 26 at one end that permits fluid flow but has a stop bar 27 to prevent the bobbin from falling out of the tube 12. At the other end, fluid flow through an opening 28 is controlled by a check valve 30 comprising a valve ball 32 biased into sealing engagement with a valve seat 34 by a spring 36. The check valve 30 prevents fluid flow to the right but permits fluid flow to the left.

Wound around the tube 12 are two coils 38 and 40, which will occasionally be referred to as coil A and coil B, respectively. A ferromagnetic collar 42 surrounds the coils 38 and 40. It includes a disk-shaped ferromagnetic separator 44 between the coils and similar disk-shaped ferromagnetic end pieces 46 and 48 at opposite ends of the coils. A ferromagnetic sleeve 50 fits over the separator 44 and end pieces 46 and 48 and is suitably fastened to them by means not shown in the drawings. The ferromagnetic collar 42 is not essential, but it is desirable because it greatly increases the sensitivity of coil mutual inductance to bobbin position.

Leads 52 extend outside of the collar 42 from coil A by means of channels provided for them between end piece 46 and the tube 12 and between end piece 46 and the sleeve 50. Leads 54 from coil B are trained in a similar manner around end piece 48.

Figure 2:
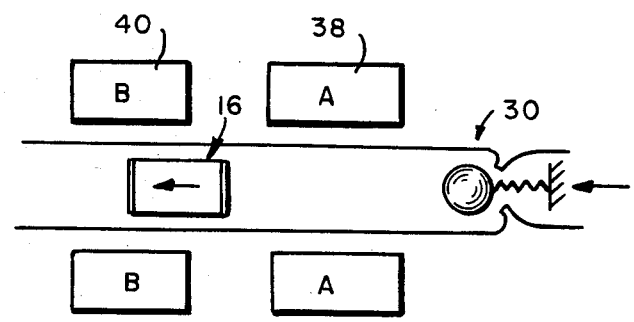
FIG. 2 is a schematic representation of the viscometer of the present invention showing the bobbin moving in the direction in which the check valve is open to permit fluid to enter.
Figure 3:
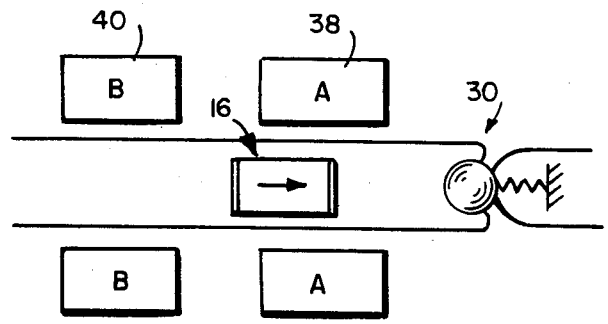
FIG. 3 is a view similar to FIG. 2 but showing the bobbin moving in the opposite direction so that the check valve is closed.

In operation, coil 40 is energized to draw the bobbin 16 toward the lowest-reluctance position near coil 40, as FIG. 2 illustrates. Movement of the bobbin 16 moves toward coil 40, i.e., to the left in FIG. 2, opens the check valve 30, and fluid is pumped into the chamber 14.

After enough time has elapsed for the bobbin to come to rest in the low-reluctance position, coil 40 is deenergized, and coil 38 is driven by a constant-amplitude alternating current. This draws the bobbin 16 to the right, allowing the spring-loaded check valve to close. As a result, the viscous force needed to balance the magnetic force is reached at a lower speed, so the speed at which the bobbin moves to the right is lower than that at which it moves to the left. The speed at which the bobbin moves to the right is inversely proportional to the viscosity of the fluid in the tube 12, so viscosity can be measured by measuring the time required for the bobbin to travel a predetermined distance.

To perform this measurement, bobbin position is sensed by monitoring the mutual inductance between the two coils 38 and 40, which changes with bobbin position. Specifically, when an electromotive force induced in coil 40 by coil 38 passes a peak and then falls back to a predetermined amplitude, timing of bobbin travel stops, and the measured time is proportional to viscosity.

Figure 4:
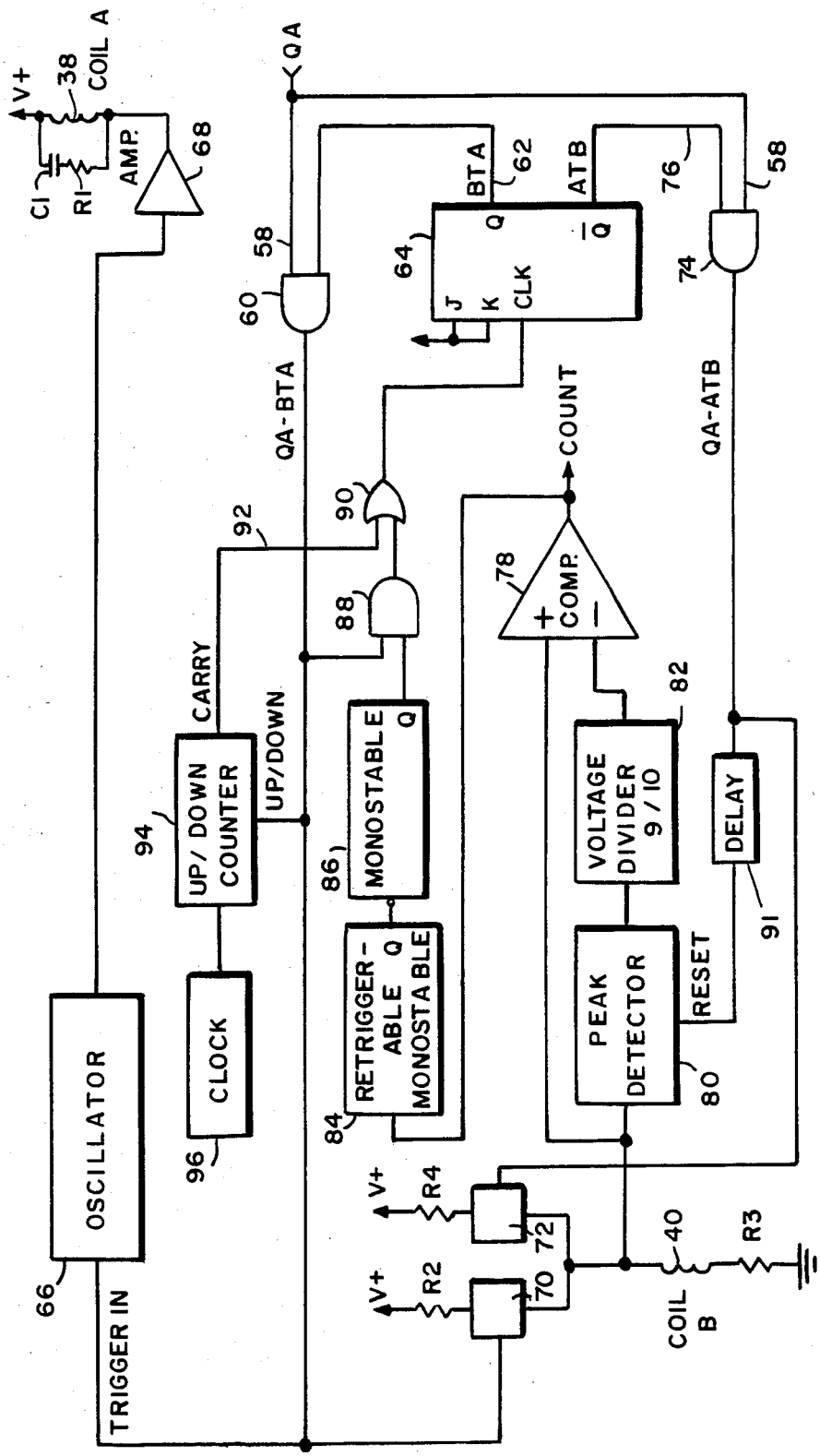
FIG. 4 is a block-diagram representation of the circuitry for driving the viscometer coils and sensing their output.
Figure 6:
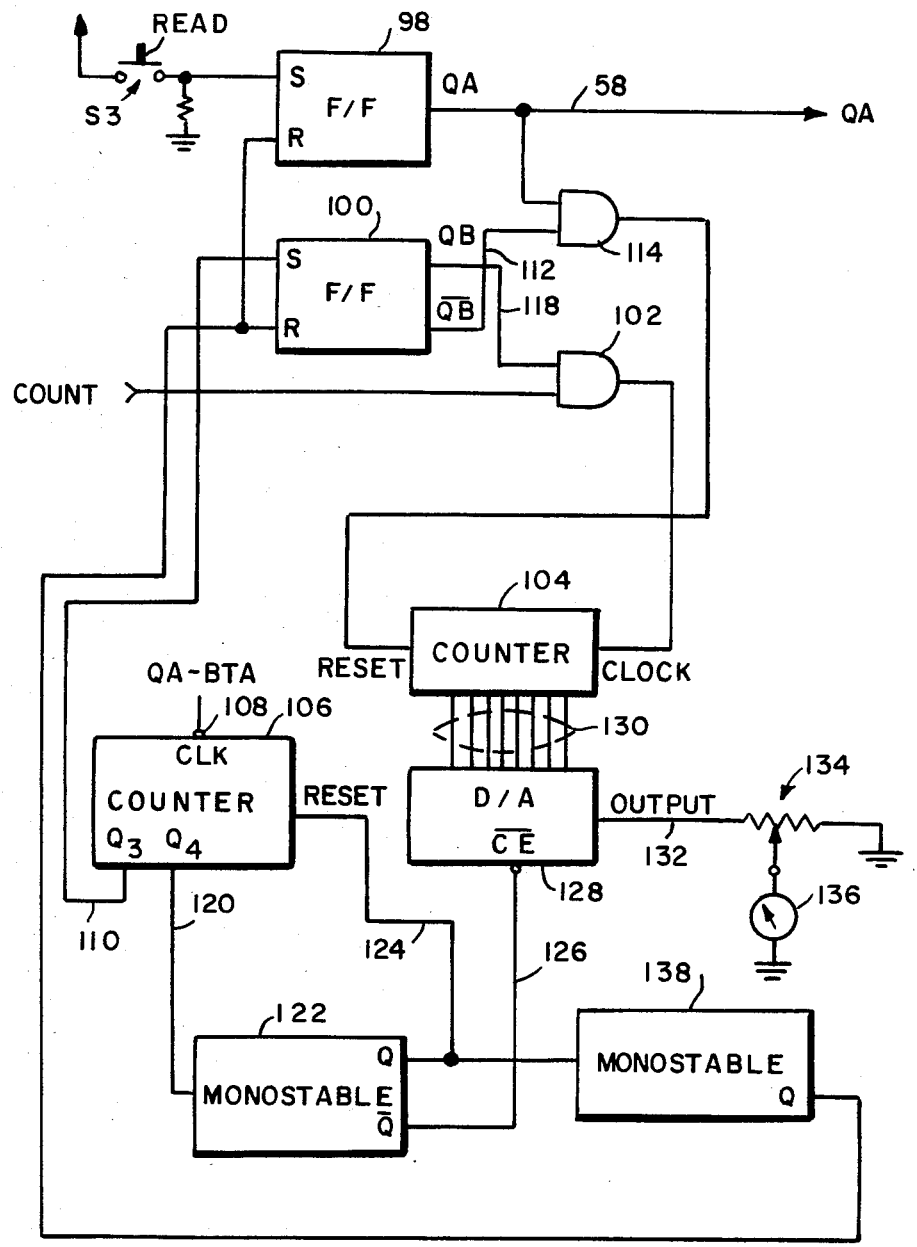
FIG. 6 is a schematic diagram of the circuitry for controlling the circuitry of FIG. 4 and for measuring the time required for the bobbin to move through the fluid.

The circuitry for driving coils 38 and 40 and monitoring their output is depicted in FIG. 4. In FIG. 4, a line 58 carrying a signal QA from timing circuitry in FIG. 6 is fed to one input terminal of an AND gate 60. A high QA signal places the circuitry in an active state, in which drive current is fed to the coils by turns. The other input to AND gate 60 is a signal on line 62 from a J-K flip-flop 64. The signal on line 62, called BTA (from coil B Toward coil A), signals that the bobbin 16 should move from coil 40 (coil B) toward coil 38 (coil A). When both QA and BTA are high—that is, when the circuit is in its active state and the bobbin 16 is to be driven to the right in FIG. 1—the output of AND gate 60 is true. This true output of gate 60 is fed to the enabling input port of an oscillator 66, which produces an oscillating signal with a period of $T_0$. This oscillating signal drives a current driver, amplifier 68, which drives coil 38 with a constant-amplitude signal; that is, the amplitude of the sinusoidal current through coil 38 is constant, although changes in its inductance can cause voltage variations. Coil 38 is shown in FIG. 4 as being wired in circuit with a resistor R1 and a capacitor C1. These are provided for snubbing.

The current in coil 40 is controlled by switches 70 and 72. Switch 70, an electronically controlled switch, provides a bias voltage so that sensing circuitry described below requires only a positive-polarity power supply. Switch 70 is closed by the high output of AND gate 60 when coil 38 is being driven, and it permits only a small bias current to flow through resistors R2 and R3 and thus through coil 40. This current does not result in a significant force on bobbin 16; it merely provides a voltage on R2 that is high enough that the voltage induced on coil 40 by coil 38 does not cause the voltage at the upper end of coil 40 to become negative.

Electronically controlled switch 72 is controlled by the output of another AND gate 74. This gate receives the high QA input on line 58 but is disabled during the B-to-A portion of the cycle because its other input, on line 76, receives the complement of the BTA signal. This complement signal is called ATB (from coil A Toward coil B) and is low during this period, so the output of AND gate 74 is also low and therefore keeps electronically controlled switch 72 open.

Figure 5A:
FIGS. 5A–5G depict waveforms at various points in the circuitry of FIG. 4.
Figure 5B:
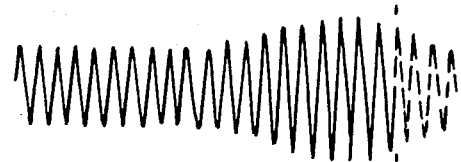

FIG. 5A illustrates the current signal applied to coil 38; it is a signal of constant current amplitude. This current induces in coil 40 an electromotive force, illustrated in FIG. 5B, that varies with the position of the bobbin 16. As FIG. 5B illustrates, the amplitude of this signal starts at an intermediate level as the bobbin is in close proximity to coil 40. The mutual inductance between the two coils increases, as does the amplitude of the induced electromotive force, as the bobbin 16 moves into the region between the coils, and the mutual inductance then reduces to a minimum as the bobbin reaches the region closest to coil 38.

Figure 5C:

The signal illustrated in FIG. 5B is present at the upper end of coil 40 in FIG. 4 and is applied both to the positive input terminal of a comparator 78 and to a peak detector 80. The peak detector 80 maintains as its output the highest voltage that it has received since it was last reset. The output of the peak detector 80 is fed to a voltage divider 82, which has an output that is nine-tenths of the magnitude of the output of the peak detector 80. This output is fed to the negative input terminal of the comparator 78. The output of the voltage divider 82 is depicted by the solid line in FIG. 5C, while the dashed line in FIG. 5C represents the envelope of the coil output depicted in FIG. 5B. Since these are the two inputs to the comparator 78, it will be appreciated that the comparator 78 will generate positive output pulses until the time represented by the intersection of the solid and dashed lines, i.e., until the output of coil 40 falls below nine-tenths of its peak magnitude. The value of nine-tenths was chosen because, in the illustrated embodiment, it corresponds to the steepest portion of the curve of mutual inductance as a function of bobbin position. This value is arbitrary, though; it is only important to be able to identify a predetermined position in the bobbin travel.

Figure 5D:
Figure 5E:

The output of the comparator 78 is fed to a retriggerable one-shot 84, whose period has been set at $2.2T_0$. So long as the output of coil 40 remains greater than 0.9 times its peak value, one-shot 84 is repeatedly retriggered before having a chance to time out, and it therefore maintains a steady high output. When the pulses from comparator 78 stop, however, indicating that the bobbin has reached the predetermined position in its travel from coil 40 toward coil 38, one-shot 84 is no longer triggered, and its output goes false at 2.2$T_0$ after the last pulse from comparator 78. The comparator output, called COUNT, is depicted in FIG. 5D, while the output of one-shot 84 is depicted in FIG. 5E. The number of pulses in the COUNT signal is proportional to the viscosity of the fluid.

Figure 5F:
Figure 5G:
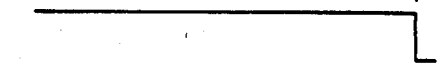

The low-going edge of the output of one-shot 86 triggers a short-duration one-shot 86, which accordingly produces a short-duration pulse, as is illustrated in FIG. 5F. This pulse signal is fed to an AND gate 88, whose other input is the high output of AND gate 60, so it forwards the pulse to an OR gate 90, whose output clocks the J-K flip-flop 64. Since both the J and the K terminals of J-K flip-flop 64 are tied to a high level, the J-K flip-flop 64 changes state, causing the BTA signal on line 62 to go from a high level to a low level, as FIG. 5G indicates.

This transition results in a change from the state in which coil 38 is energized to that in which coil 40 is energized. Specifically, the low value of BTA on line 62 disables AND gate 60 so that it in turn disables the oscillator 66 and thereby terminates the drive current applied to coil 38. At the same time, the ATB signal on line 76 goes high, enabling AND gate 74 to forward the high QA signal to electronically controlled switch 72, closing it and permitting a relatively high current to flow through a low resistance R4 and thus through coil 40. The resultant magnetic field draws the bobbin 16 to the left in FIG. 1. At the same time, electronically controlled switch 70 opens because it is controlled by the now low output of AND gate 60.

The high-going output of AND gate 74 is also fed to a delay circuit 91, which forwards this signal after a short delay to the reset terminal of peak detector 80 to cause its output to return to a zero-voltage level. The high reset input keeps the peak-detector output at a zero-voltage level until the reset input goes low again in response to the beginning of the next B-to-A cycle, when the output of AND gate 74 goes low. The delay circuit 91 delays the removal of the reset input so that the peak detector 80 does not record transients caused by the changes of state of switches 70 and 72.

The resistances of R3 and R4 are arranged so that the force on the ferromagnetic bobbin 16 caused by coil 40 when it is energized is roughly equivalent to the force applied by coil 38 when it is energized, and this force is applied for the same length of time as that applied by coil 38. The bobbin 16 travels to the left much more quickly than it travels to the right, though, because the check valve 30 permits fluid flow to the left in FIG. 1, so the bobbin 16 encounters much less viscous resistance for a given speed in moving to the left than it did in moving to the right and therefore travels much more quickly. The bobbin thus has time to come to rest in the low-reluctance position adjacent to coil 40.

The A-to-B portion of the cycle ends when the J-K flip-flop 64 is clocked by the carry output on line 92 from an up/down counter 94 that counts pulses from a free-running clock 96. The up/down counter 94 is controlled by the output of AND gate 60; it counts up from zero during the B-to-A portion of the cycle, when the AND gate 60 output is high, and it counts back down to zero during the A-to-B portion of the cycle, when the output of AND gate 60 is low. When counter 94 passes a count of zero in counting down, the A-to-B portion of the cycle has lasted as long as the B-to-A portion, and a pulse is produced in the carry output on line 92. OR gate 90 forwards this pulse to the clock terminal of the J-K flip-flop 64 so that coil 38 is energized again and coil 40 is de-energized.

As was stated above, the QA signal on line 58 is an indication that the viscometer 10 should be active. The QA signal is the output of an R-S flip-flop 98, which is depicted in FIG. 6 as being set by operation of a switch S1. It is not necessary that this flip-flop 98 be set manually, however, and it could be set automatically at periodic intervals by a digital signal sent from some other device.

A high QA signal indicates an active state, in which the bobbin 16 is driven back and forth as was previously described. A low QA signal indicates an inactive state, in which the bobbin 16 remains at rest. In the active state, there are two modes. In one mode, the bobbin moves to the left in FIG. 1 to draw more fluid into the chamber 14 and then moves to the right in FIG. 1 against viscous resistance, its transit time in moving to the right being measured by accumulating COUNT pulses, as will be described below. In the other mode, the bobbin 16 moves to the left and to the right as in the first mode, but the motion has the sole purpose of pumping new fluid into the chamber 14 before measurement to ensure that the sample inside the tube 12 is representative. In this mode, therefore, no count is performed.

The setting of the mode—i.e., the purge mode or the measurement mode—is performed by a further R-S flip-flop 100, which normally is in the reset condition when the active state begins. In this reset condition, its QB output on line 101 is low to indicate that the circuit is not in the measurement mode. This QB signal is fed to an AND gate 102 to prevent it from forwarding the COUNT signal to a counter 104 that times bobbin travel duration during the measurement mode. During the purge mode, the counter 104 therefore does not accumulate COUNT pulses and thus does not time bobbin travel. Since the QA signal is high, however, the bobbin 16 still moves back and forth, pumping fluid into the chamber 14 and thereby updating the sample fluid.

The number of times that the bobbin 16 cycles back and forth during the purge mode is counted by a counter 106, which receives at its clock terminal 108 the output of AND gate 60. Whenever the B-to-A portion of the bobbin travel ends, the low-going output signal from AND gate 60 clocks counter 106. When counter 106 reaches a count of 8, its $Q_3$ output line 110 goes high and sets the mode flip-flop 100, whose QB-complement signal on line 112 goes low, causing an AND gate 114 to drop the reset signal that it had been applying to counter 104. At the same time, the QB output signal goes high, thereby enabling AND gate 102 to forward the COUNT signal to counter 104. Counter 104 accordingly begins counting the COUNT pulses that the comparator 78 (FIG. 4) generates during the B-to-A portions of the active state.

Since counter 104 counts only during these periods, its count is proportional to the time required for the bobbin 16 to move a predetermined distance through the fluid. Thus, the count in counter 104 after one left-to-right cycle of the bobbin 16 is proportional to the viscosity of the fluid.

In order to reduce quantization and other random errors, however, the count in counter 104 is assembled over, say, eight cycles. The cycle counter 106, which reached the count of 8 to begin the measurement mode, continues counting cycles during the measurement mode. When it reaches a count of 16, its $Q_4$ output on line 120 becomes true and triggers a one-shot 122, whose resultant output on line 124 resets counter 106. The low-going complement output of one-shot 122 is fed over line 126 to a digital-to-analog converter 128, which receives in parallel the output of counter 104 over lines 130. The signal on line 126 causes the digital-to-analog converter 128 to latch in the value on lines 130 and present an analog output on line 132 to a potentiometer 134. This potentiometer scales the analog output signal and presents the result to an analog indicator 136. In the alternative, of course, the digital value on lines 130 could be latched and displayed in a digital manner.

When one-shot 122 times out, it triggers a further one-shot 138, which causes the state and mode flip-flops 98 and 100 to reset, stopping the cycling of the viscometer and returning it to its generally inactive state until switch S1 is activated again.

It is apparent that the illustrated viscometer is distinguished by its simplicity of fabrication and use. The simplicity results in large measure from the fact that several parts perform more than one function. The bobbin acts both as a viscosity probe and as a pump element. The check valve acts both to increase viscous resistance during measurement and to insure that fluid flows in the proper direction during purging. The coils act as means for driving the bobbin during measurement, as means for driving the bobbin during purging, and as means for sensing bobbin position. As a result, the viscometer has only two moving parts, the bobbin and the check valve, and it is thus quite reliable. It is simple to use because it requires no separate filling operation; the purging mode, which causes a new sample to be drawn into the chamber, is mechanically the same as the measuring mode. Furthermore, because the bobbin is of substantially neutral buoyancy, the operation of the viscometer is substantially insensitive to orientation and vibration.

Although the viscometer described above embodies many different features of the present invention, various of the advantages of the invention can be obtained without using all of its aspects. For instance, although a check valve is advantageously employed in the illustrated viscometer both to increase viscous resistance and to aid in purging by permitting fluid flow in only one direction, a viscometer without a check valve would still afford some of the advantages of the illustrated viscometer. Clearly, replacement of the fluid sample would not be nearly as efficient without the check valve, and the viscous force used in measuring viscosity would not be as great without some means to restrict fluid flow during measurement, but these factors may not be important in some applications.

The neutral buoyancy of the bobbin, although particularly beneficial in applications in which vibration and orientation changes can be expected, may not be as important in some other situations. Indeed, if a known orientation can be guaranteed, it may be preferred to employ gravity to drive the bobbin in one direction or the other. The use of a coil to drive the bobbin in the other direction, and the sensing of position by monitoring inductance, would still be beneficial.

Furthermore, the magnetic driving of the bobbin and the position sensing by inductance monitoring do not require two coils. I prefer two coils because mutual inductance is relatively sensitive to bobbin position in the illustrated configuration. But the self-inductance of the driving coil is also a function of bobbin position, and it can therefore be used to sense position. Additionally, a single coil could be used to drive the bobbin in both directions. If the bobbin contained a permanent magnet in addition to the ferromagnetic material, DC components of opposite polarity in the coil drive signal could achieve this result. Indeed, the benefits afforded by a neutrally buoyant bobbin and the check valve can be obtained even in a viscometer with no coils, in which the bobbin is not driven magnetically and position sensing is not performed by monitoring inductance.

Accordingly, the teaching of the present invention can be employed in a wide variety of viscometer types.

I claim:

1. A viscometer comprising:
   A. a bobbin including ferromagnetic material;
   B. guide means for guiding the bobbin between first and second positions through a fluid whose viscosity is to be measured;
   C. bobbin-driving means for driving the bobbin from the first position to the second position with a predetermined force;
   D. first and second coils disposed adjacent the guide means and oriented with respect thereto so that the mutual inductance between the first and second coils changes as a function of bobbin position; and
   E. means for monitoring the mutual inductance, measuring the time from the time at which the bobbin leaves the first position to the time at which the monitored inductance reaches the point in its position function that corresponds to the second position, and generating an indication of that time measurement, thereby indicating the viscosity of the fluid.

2. A viscometer as defined in claim 1 wherein the monitoring means includes:
   A. a current driver for driving the first coil with an alternating current of constant amplitude to induce an alternating voltage in the second coil whose amplitude changes as a function of bobbin position;
   B. means for monitoring the voltage induced in the second coil, measuring the time from the beginning of bobbin travel from the first position to the time at which the amplitude of the monitored voltage reaches the point in its position function that corresponds to the second position, and generating an indication of that time measurement, thereby indicating the viscosity of the fluid.

3. A viscometer as defined in claim 2 wherein the bobbin-driving means includes the first coil and a current driver for driving current through the coil to generate a magnetic field that draws the ferromagnetic bobbin through the fluid from the first position to the second position.

4. A viscometer as defined in claim 3 wherein the bobbin is substantially neutrally buoyant.

5. A viscometer as defined in claim 5 wherein the bobbin-driving means further drives the bobbin from the second position to the first position and includes the second coil and a current driver for driving current through the second coil to generate a magnetic field that draws the ferromagnetic bobbin through the fluid from the second position to the first position.

6. A viscometer as defined in claim 5 wherein:
   A. the guide means comprises means forming a chamber for containing the fluid and in which the bobbin is disposed, the chamber-forming means having an inlet and an outlet;
   B. the viscometer further includes a unidirectional valve for permitting fluid to flow in through the inlet, through the chamber, and out through the outlet but preventing fluid from flowing in through the outlet, through the chamber, and out through the inlet; and C. motion of the bobbin from the second position to the first position tends to draw fluid in the inlet, through the chamber, and out through the outlet, whereby the contents of the chamber tend to be refreshed in response to driving of the second coil.

7. A viscometer as defined in claim 1 wherein the bobbin-driving means includes the first coil and a current driver for driving current through the coil to generate a magnetic field that draws the ferromagnetic bobbin through the fluid from the first position to the second position.

8. A viscometer as defined in claim 7 wherein the bobbin-driving means further drives the bobbin from the second position to the first position and includes the second coil and a current driver for driving current through the second coil to generate a magnetic field that draws the ferromagnetic bobbin through the fluid from the second position to the first position.

9. A viscometer as defined in claim 1 wherein the bobbin-driving means includes one of the coils and a current driver for driving current through the coil to generate a magnetic field that draws the ferromagnetic bobbin through the fluid from the first position to the second position.

10. A viscometer as defined in claim 8 wherein:
A. the guide means comprises means forming a chamber for containing the fluid and in which the bobbin is disposed, the chamber-forming means having an inlet and an outlet;
B. the viscometer further includes a unidirectional valve for permitting fluid to flow in through the inlet, through the chamber, and out through the outlet but preventing fluid from flowing in through the outlet, through the chamber, and out through the inlet; and
C. motion of the bobbin from the second position to the first position tends to draw fluid in the inlet, through the chamber, and out through the outlet, whereby the contents of the chamber tend to be refreshed in response to driving of the second coil.

11. A viscometer comprising:
A. a bobbin including ferromagnetic material;
B. guide means for guiding the bobbin between first and second positions through a fluid whose viscosity is to be measured;
C. bobbin-driving means for driving the bobbin from the first position to the second position with a predetermined force;
D. first and second coils disposed adjacent the guide means and oriented with respect thereto so that the mutual inductant between the first and second coils changes as a function of bobbin position;
E. a current driver for driving the first coil with an alternating current of constant amplitude to induce an alternating voltage in the second coil whose amplitude changes as a function of bobbin position; and
F. means for monitoring induced coil voltage; measuring the time from the time at which the bobbin leaves the first position to the time at which the amplitude of the monitored voltage reaches the point in its position function that corresponds to the second position, and generating an indication of that time measurement, thereby indicating the viscosity of the fluid.

12. A viscometer comprising:
A. chamber-forming means forming a chamber, having an inlet and an outlet, for containing a fluid whose viscosity is to be measured;
B. a bobbin disposed in the chamber;
C. bobbin-driving means for driving the bobbin from a first position to a second position with a predetermined force and for driving the bobbin from the second position to the first position, motion of the bobbin from the second position to the first position tending to draw fluid in the inlet, through the chamber, and out through the outlet;
D. means for measuring the time required for the bobbin to travel from the first position to the the second position and generating an indication of that time measurement, thereby indicating the viscosity of the fluid in the chamber; and
E. a unidirectional valve for permitting fluid to flow in through the inlet, through the chamber, and out through the outlet but preventing fluid from flowing in through the outlet, through the chamber and out through the inlet, whereby the contents of the chamber tend to be refreshed in response to driving of the bobbin from the second position to the first position.

13. A viscometer as defined in claim 12 wherein the bobbin-driving means includes a coil and a current driver for driving current through the coil to generate a magnetic field that draws the ferromagnetic bobbin through the fluid from the first position to the second position.

14. A viscometer as defined in claim 13 wherein the bobbin-driving means includes a second coil and a current driver for driving current through the second coil to generate a magnetic field that draws the ferromagnetic bobbin through the fluid from the second position to the first position.

15. A viscometer as defined in claim 14 wherein the bobbin is substantially neutrally buoyant.

16. A viscometer as defined in claim 13 wherein the bobbin is substantially neutrally buoyant.

17. A viscometer as defined in claim 12 wherein the bobbin is substantially neutrally buoyant.

18. A method of measuring the viscosity of a fluid comprising the steps of:
A. providing a bobbin in the fluid having substantially neutral buoyancy with respect thereto;
B. applying a predetermined force to the bobbin to move it a predetermined distance through the fluid; and
C. measuring the time required for the bobbin to travel the predetermined distance, the time measurement thereby being an indication of the viscosity of the fluid and being substantially insensitive to the direction of movement of the bobbin with respect to gravity.

19. A viscometer as recited in claim 7 wherein:
A. the guide means comprises means forming a chamber for containing the fluid and in which the bobbin is disposed, the chamber-forming means having an inlet and an outlet; and
B. the viscometer further includes a unidirectional valve for permitting fluid to flow in through the inlet, through the chamber, and out through the outlet but preventing fluid from flowing in through the outlet, through the chamber, and out through the inlet, whereby motion of the bobbin from the second position to the first position tends to draw fluid in the inlet, through the chamber, and out through the outlet so that the contents of the chamber tend to be refreshed between movements of the bobbin from the first position to the second position.

20. A viscometer as defined in claim 1 wherein the guide means guides the bobbin along a bobbin path between the first and second positions and the first and second coils are spaced from each other along the bobbin path.

21. A viscometer as defined in claim 2 wherein the guide means guides the bobbin along a bobbin path between the first and second positions and the first and second coils are spaced from each other along the bobbin path.

22. A viscometer as defined in claim 3 wherein the guide means guides the bobbin along a bobbin path between the first and second positions and the first and second coils are spaced from each other along the bobbin path.

23. A viscometer as defined in claim 7 wherein the guide means guides the bobbin along a bobbin path between the first and second positions and the first and second coils are spaced from each other along the bobbin path.

* * * * *

UNITED STATES PATENT AND TRADEMARK OFFICE
CERTIFICATE OF CORRECTION

PATENT NO. : 4,627,272

DATED : December 9, 1986

INVENTOR(S) : Hubert A. Wright

It is certified that error appears in the above-identified patent and that said Letters Patent is hereby corrected as shown below:

Column 8, line 55, replace "5" after "claim" with --4--.

Signed and Sealed this

Twenty-fifth Day of August, 1987

Attest:

DONALD J. QUIGG

Attesting Officer      Commissioner of Patents and Trademarks